United States Patent [19]

Pews

[11] Patent Number: 4,493,929

[45] Date of Patent: Jan. 15, 1985

[54] PREPARATION OF 2-ALKYLPYRIMIDINES

[75] Inventor: Richard G. Pews, Midland, Mich.

[73] Assignee: The Dow Chemical Company, Midland, Mich.

[21] Appl. No.: 458,812

[22] Filed: Jan. 18, 1983

Related U.S. Application Data

[63] Continuation-in-part of Ser. No. 301,684, Sep. 14, 1981, abandoned.

[51] Int. Cl.³ .......................................... C07D 239/26
[52] U.S. Cl. ............................................................ 544/242
[58] Field of Search ........................................ 544/242

[56] References Cited

U.S. PATENT DOCUMENTS

| | | | |
|---|---|---|---|
| 2,658,895 | 11/1953 | Ballard et al. | 544/242 |
| 3,050,523 | 8/1962 | Erner et al. | 544/242 |
| 4,376,201 | 3/1983 | Pews | 544/242 |

FOREIGN PATENT DOCUMENTS

| | | | |
|---|---|---|---|
| 2701372 | 7/1978 | Fed. Rep. of Germany | 544/242 |

OTHER PUBLICATIONS

Germain, "Catalytic Conversion of Hydrocarbons", Academic Press, London & New York (1969), pp. 102–107.

Tsuchiya, et al., Chemical Abstracts, vol. 87, 84049e (1977).

Lythgoe, et al., J. Chem. Soc. 1951, pp. 2323–2329 (1951).

"The Pyrimidines", Interscience Publishers (1962), pp. 445–448, 455.

Okada, et al., Chemical Abstracts, vol. 85, 142251m (1976).

Tsuchiya, et al., Chemical Abstracts, vol. 86, 29475h (1977).

Disteldorf, et al., Chemical Abstracts, vol. 89, 180044m (1978).

*Primary Examiner*—Donald G. Daus
*Assistant Examiner*—Diana G. Rivers

[57] ABSTRACT

2-Alkylpyrimidines are obtained in a one step reaction which comprises the dehydrogenation of a 2-alkyltetrahydropyrimidine over a supported noble metal catalyst under conditions which do not generate water and in which no water is added.

5 Claims, No Drawings

PREPARATION OF 2-ALKYLPYRIMIDINES

REFERENCE TO RELATED APPLICATIONS

This application is a continuation-in-part of Ser. No. 301,684 filed Sept. 14, 1981, now abandoned.

BACKGROUND OF THE INVENTION

The preparation of 2-alkylpyrimidines is taught in U.S. Pat. No. 3,050,523. That process requires the reaction of an alkylene 1-3 diamine with an organic carboxylic acid, ester or amide over supported noble metal catalysts having dehydration and dehydrogenation activity. The desired compounds may be obtained by azeotropic distillation or by treatment with carbon dioxide followed by distillation. The work-up procedures are time consuming and the yields are not as good as could be desired.

Lythgoe et al., J. Chem. Soc. 1951, pp. 2323-2329 teach the dehydrogenation of tetrahydro-2-phenylpyrimidine in a current of carbon dioxide.

SUMMARY OF THE INVENTION

I have now found that 2-alkylpyrimidines can be obtained in high yields and purity in a simple one step reaction which comprises the dehydrogenation of a 2-alkyltetrahydropyrimidine under conditions which do not generate water and in which no water is added over a supported noble metal catalyst.

DETAILED DESCRIPTION OF THE INVENTION

The reaction may be carried out neat, i.e., without employing a solvent, although an inert solvent such as, for example, pyridine may be advantageously employed.

The preferred catalysts are platinum and palladium which are supported on, for example, silica gel, charcoal, activated carbon, magnesia or, preferably, alumina.

The reaction temperature is in the range of 250° to 450° C., preferably 300° to 400° C. Advantageously, the desired tetrahydropyrimidine, with or without solvent, is passed through a packed column containing the supported noble metal catalyst heated to the desired temperature. Feed rates to the vapor phase reactor, a 1"×20" column containing 50 g of catalyst, are 20 to 150 ml/hr, preferably 40 to 80 ml/hr.

To avoid the generation of water in the presence of hydrogen it is necessary that oxygen be excluded from the reaction zone. The exclusion of oxygen is preferably accomplished by sweeping out the reactor with an inert gas, e.g. nitrogen or carbon dioxide. If desired, the inert gas may contain hydrogen gas which serves to activate the catalyst. In any event, hydrogen will be present as the dehydrogenation reaction proceeds.

The invention is further illustrated by the following examples.

EXAMPLE 1

A solution of 70 g of 2-isopropyl-1, 4, 5, 6-tetrahydropyrimidine in 100 ml of pyridine was fed at about 1 ml/min to a column 1"×20" containing about 50 g of 0.5 percent platinum on α-alumina at 300° to 325° C. while sweeping out the column with a mixture of nitrogen and hydrogen. The catalyst had been activated by passing a 2:1 $H_2/N_2$ stream over the bed for two hours. The effluent was distilled giving 2-isopropylpyrimidine at 152° to 155° C. The yield was 73 percent.

The above example was repeated employing varying amounts of 2-tertiarybutyl-1,4,5,6-tetrahydropyrimidine, varying amounts of solvents, 0.5 percent palladium on alumina and temperatures of from 250° to 420° C. The yields of 2-tertiarybutylpyrimidine ranged from 58 to 86 percent.

Similar results are obtained employing other solvents such as, for example, quinoline.

EXAMPLE 2

91.6 g of 2-isopropyl-1,4,5,6-tetrahydropyrimidine was fed dropwise to the vapor phase dehydrogenator (1"×20") with 50 g of 0.5 percent palladium on α-alumina over a two hour period while sweeping out the dehydrogenator with a stream of nitrogen and hydrogen. The reactor temperature was 310° C. The product was distilled to give 67 g of product, b.p. 155° C., yield 86 percent.

In a similar manner, 2-methyl- and 2-ethylpyrimidine were also prepared in good yields and purity.

Various modifications may be made in the present invention without departing from the spirit or scope thereof and it is understood that I limit myself only as defined in the appended claims.

I claim:

1. A process for making 2-alkylpyrimidines which comprises dehydrogenating a 2-isopropyl- or 2-tertiarybutyltetrahydropyrimidine in a vapor phase reactor in the absence of oxygen and in which no water is added over a supported noble metal catalyst.

2. Process of claim 1 wherein the reaction is carried out at 250° to 450° C.

3. Process of claim 2 wherein the temperature is 300° to 400° C.

4. Process of claim 3 wherein the catalyst is platinum or palladium.

5. Process of claim 4 wherein the catalyst is supported on alumina.

* * * * *